US009051533B2

(12) United States Patent
Kellens et al.

(10) Patent No.: US 9,051,533 B2
(45) Date of Patent: Jun. 9, 2015

(54) CONTINUOUS FRACTIONATION OF TRIGLYCERIDE OILS

(71) Applicant: n.v. Desmet Ballestra Engineering s.a., Zaventem (BE)

(72) Inventors: Marc Kellens, Mechelen-Muizen (BE); Gijs Calliauw, Onze-Lieve-Vrouw-Lombeek (BE); Marc Hendrix, Balen (BE)

(73) Assignee: n.v. DESMET BALLESTRA ENGINEERING s.a., Zaventem (BE)

( * ) Notice: Subject to any disclaimer, the term of this patent is extended or adjusted under 35 U.S.C. 154(b) by 281 days.

(21) Appl. No.: 13/675,016

(22) Filed: Nov. 13, 2012

(65) Prior Publication Data

US 2013/0123524 A1 May 16, 2013

(30) Foreign Application Priority Data

Nov. 15, 2011 (GB) .................................. 1119680.5

(51) Int. Cl.
*C07C 51/43* (2006.01)
*C11B 3/00* (2006.01)
*C11C 1/00* (2006.01)
*C11B 7/00* (2006.01)

(52) U.S. Cl.
CPC ................. *C11B 3/008* (2013.01); *C11C 1/005* (2013.01); *C11B 7/0075* (2013.01)

(58) Field of Classification Search
CPC ...... C11B 7/0075; C11B 7/0083; C11C 1/005
USPC .......................................................... 554/211
See application file for complete search history.

(56) References Cited

U.S. PATENT DOCUMENTS

| | | | |
|---|---|---|---|
| 4,127,597 | A | 11/1978 | Craig, Jr. et al. |
| 4,542,036 | A | 9/1985 | Maes et al. |
| 4,594,259 | A | 6/1986 | Baker et al. |
| 4,839,191 | A | 6/1989 | Luddy et al. |
| 5,198,123 | A | 3/1993 | Stover et al. |
| 5,874,599 | A | 2/1999 | Harris et al. |
| 6,383,456 | B1 | 5/2002 | Hartel et al. |

FOREIGN PATENT DOCUMENTS

| | | | | | |
|---|---|---|---|---|---|
| EP | 1 028 159 | A1 | | 8/2000 | |
| EP | 1 281 749 | A1 | | 2/2003 | |
| EP | 1281749 | A1 | | 2/2003 | |
| EP | 1 818 088 | A1 | | 8/2007 | |
| EP | 1 889 898 | A1 | | 2/2008 | |
| GB | 2 053 019 | A | | 2/1981 | |
| GB | 2 458 694 | A | | 9/2009 | |
| GB | 2458694 | A | * | 9/2009 | ............... B01D 9/00 |
| JP | 56005104 | A | | 1/1981 | |
| WO | WO 96/05279 | A1 | | 2/1996 | |

OTHER PUBLICATIONS

Search Report Linder Section 17(5) issued by the Intellectual Property Office in Britain mailed Mar. 9, 2012 for Application No. GB1119680.5 filed Nov. 15, 2011.

GB Examination Report Under Section 18(3) issued by the Intellectual Property Office in Britain mailed Aug. 20, 2013 for Application No. GB1119680.5 filed Nov. 15, 2011.

* cited by examiner

*Primary Examiner* — Deborah D Carr

(74) *Attorney, Agent, or Firm* — Wegman, Hessler & Vanderburg

(57) ABSTRACT

A continuous process for the dry fractionation of edible oils and fats using one or more crystallisers in series, said process comprising the steps of: (a) providing a molten fat; (b) continuously feeding said molten oil or fat to the first of said one or more crystallisers in series in which the fat is gradually cooled by using heat exchangers containing a cooling medium so that a crystal slurry is formed, each of said one or more crystallisers exhibiting a temperature gradient, the temperature at the point where the molten or partially crystallised fat enters one of the crystallisers being higher than that at the point where the slurry leaves that crystalliser; (c) continuously withdrawing said slurry from the last of said one or more crystallisers; (d) separating said crystal slurry by filtration in a filter cake and a filtrate, wherein said process further comprises the step of at least partially melting fat encrustations deposited on said heat exchangers; and an oil fraction produced by therefrom.

19 Claims, No Drawings

CONTINUOUS FRACTIONATION OF TRIGLYCERIDE OILS

FIELD OF THE INVENTION

The invention relates to the modification of edible oils and fats by continuous fractionation in the absence of organic solvents.

BACKGROUND OF THE INVENTION

The physical properties of edible oils and fats as obtained from agricultural sources do not necessarily correspond to the requirements of the food industry.

Consequently, several modification processes have been developed. In the hydrogenation process, a liquid oil is converted into a solid fat that can be used as hardstock in margarines and shortenings and at the same time increases its stability. In the interesterification process, physical properties of the material being interesterified are modified for instance by lowering its melting point and thereby avoiding a sticky mouthfeel. These processes modify an oil or oil blend and yield a single product. The fractionation process on the other hand separates the oil or fat in a higher melting stearin fraction and a lower melting olein fraction, each of which can yield further products by subsequent fractionation. Accordingly, the range of oil and fat products that can be produced by fractionation is very wide.

Various fractionation processes have been developed for edible oils and fats. Solvent fractionation processes use solvents such as acetone, nitropropane or hexane, but since these solvents are inflammable, their use requires an explosion-proof plant, which is expensive. Further expense is incurred by the removal of the solvent from the various fractions by distillation and by solvent loss. Accordingly, the solvent fractionation process is only used for the production of high-value specialities. There is also the detergent fractionation process but as a result of the improvements in the dry fractionation process, the detergent fractionation process can be regarded as superseded.

In dry fractionation, it is customary to heat the fat to be fractionated to about 10° C. above its melting point to erase crystal memory. The fat is then cooled slowly to below its melting point, whereupon crystals are formed and grow. When a sufficient degree of crystallisation has been attained, the crystal slurry is separated by filtration into a filter cake (the stearin), and a filtrate (the olein). Two types of crystallisation process are used. There is the process in which the melt is dispensed in trays and is not agitated during cooling. Such a process has been disclosed in EP 1 028 159A and can be advantageously used for oils such as palm kernel oil. The other type that is used for palm oil, anhydrous milk fat and various other oils, fats and butters employs large crystallisation vessels that are fitted with heat exchangers and an agitator.

Both types have in common that the filtration efficiency determines the yield of both fractions and the properties of the stearin. If the residual olein content of the filter cake is high, the stearin yield is high but the stearin properties are less extreme. Since in palm oil fractionation, the olein has a higher economic value than the palm stearin and the stearin economic value hardly depends on its properties, it is advantageous to aim for maximum filtration efficiency. This can be attained by using a membrane filter press in a batch process as disclosed in U.S. Pat. No. 5,198,123. A continuous filtration process employing a conical sieve centrifuge fitted with a co-rotating scroll has been disclosed in U.S. Pat. No. 4,542,036.

With the increasing production of palm oil, dry fractionation processes have become very important. Palm olein is a valuable cooking oil, palm oil mid fractions being used in confectionery applications, and palm stearin is used more and more as a component in the interesterification reaction mixtures used for the production of trans-free hardstocks for margarines and shortenings. Often these dry fractionation processes are integrated in palm oil refineries so that they can share the utilities and infrastructure. These refinery processes, such as degumming, bleaching and physical refining, are all continuous processes and differ in this respect from current fractionation processes, which are invariably batch processes.

Continuous fractionation processes have been developed starting from solvent fractionation processes. U.S. Pat. No. 4,127,597 discloses a process for fractionating tallow into three distinct fractions, a hard, high-melting solid fraction, a plastic solid having physical and thermal properties similar to those of cocoa butter, and a liquid oil fraction, comprising: (a) dissolving the tallow in a suitable solvent, the ratio of solvent to tallow being sufficient to solubilize the tallow and to effect a fractionation at a crystallizable ratio of solute concentration and temperature; (b) feeding, continuously, the solution to one or more crystallizers; (c) circulating the solution through the crystallizers at a first preselected steady state crystallization temperature range; (d) limiting the nominal residence time of said solution in the crystallizers at said first steady state crystallization temperature to a maximum of ten minutes; (e) crystallizing out a hard, high-melting solid thereby forming a circulating crystallized stream; (f) withdrawing continuously part of said crystallized stream at said first preselected steady state crystallization temperature to obtain crystallized hard, high-melting solid and filtrate; (g) recirculating, continuously, at said first preselected steady state crystallization temperature, the crystallized stream not withdrawn in step (f) together with aforesaid continuously fed solubilized tallow; (h) repeating steps (f) and (g) until all of the solubilised tallow is fed to the crystallizers and all of said crystallized stream is withdrawn from the crystallizers; (i) circulating the filtrate from the aforesaid first crystallization through said crystallizers at a second preselected steady state crystallization temperature range; (j) limiting the nominal residence time of said filtrate solution in the crystallizers at the steady state crystallization temperature to a maximum of 10 minutes; (k) crystallizing out a plastic solid having physical and thermal properties similar to those of cocoa butter thereby forming a circulating crystallized stream; (l) withdrawing continuously part of said crystallized stream at said second preselected steady state crystallization temperature to obtain crystallized plastic solid and filtrate; (m) recirculating, continuously, at said second preselected steady state crystallization temperature, the crystallized stream not withdrawn in step (l); (n) repeating steps (l) and (m) until all of said crystallized stream is withdrawn from the crystallizers; and (o) removing the solvent from the filtrate from the aforesaid second crystallization to obtain a liquid oil fraction. According to U.S. Pat. No. 4,594,259, suitable confectionery fats can be obtained by continuous fractionation of palm oil when using an acetone/fat ratio of about 5:1 to about 8:1 and employing two or more fractionation stages.

U.S. Pat. No. 4,839,191 discloses a process for the solvent fractionation of fats into at least two fractions including a first high melting glyceride fraction and a second fraction that is an oil at temperatures above 10° C., the process comprising the steps of: (a) dissolving the fat in a solvent which is a binary azeotropic solvent mixture, the solvent ratio being from 1.5 to 8.0 ml of solvent per gram of fat; (b) crystallizing the solution from step (a) at 10° C.-15° C.; (c) separately collecting a solvent phase and the precipitate formed in step (b); (d) extracting the precipitate of step (c) by contacting with fresh solvent cooled to about 2° C. below the temperature of step (b) using at least about 8% of the original volume of solvent; (e) collecting a solvent phase and a precipitate from step (d), which precipitate is a hard fat fraction having a melting point above 40° C.; and (f) combining the solvent phases from step (c) and step (e) and eliminating solvent therefrom to provide an oil fraction which is liquid above 10° C. This process can be performed either as a batch or as a continuous process.

The favouring of the use of solvents is quite understandable, since fats crystallise much faster from a solvent such as acetone than from the melt. In addition, the solvent dilutes the olein present in the filter cake so that for a given filtration efficiency, the stearin contains less olein resulting in its properties being less affected by olein than in the absence of the solvent. Moreover, the solvent fractionation processes listed above date from before the development of the current, efficient filtration systems employing for instance a membrane filter press.

Apart from these technological reasons, there are also physico-chemical ones. The fractional crystallisation of fats from a melt is a very complex process, because fats are mixtures of many different triacylglycerol molecules. Accordingly, the fat crystals formed during fractionation are mixed crystals containing several different molecular entities and moreover, their compositions evolve as the crystallisation proceeds. In this respect, the fractional crystallisation of fats differs fundamentally from other industrial crystallisation processes as used for instance for p-xylene, terephthalic acid, sugar, citric acid, etc. These processes are primarily purification processes that aim at the formation of pure crystals. Another factor complicating fat crystallisation is that fat crystals can have different morphologies and the crystallisation conditions must be such that only a single polymorph is formed. In addition, oils and fats—and this is particularly true for palm oil—invariably contain partial glycerides such as diacylglycerols that affect crystal growth, which may attach themselves to a growth site on the crystal and temporarily hinder the attachment of further triglyceride entities.

U.S. Pat. No. 5,874,599 discloses a process for the crystallisation of polymorphic fat molecules in a pseudo-steady state process, wherein the crystallisation is performed in a dry fractionation system by selecting and adjusting the flow rate, shear rate and temperature in such a way that the crystal form of the product is a kinetically-stable crystal form, while during the crystallisation a σ-value is maintained below 0.5, during a period of at least 12 hrs, wherein: $\sigma=1-S_c/S_E$, where $S_c$ is the percentage of solids in the crystalliser at the crystallisation temperature and $S_E$ is the percentage after stabilisation for 48 hours at the exit temperature of the crystalliser. The process uses a single crystalliser in which the crystallisation degree is close to equilibrium (solubility). When palm olein was used as starting material, the fractionation process yielded about equal amounts of top and bottom fractions and could be continued for 60-70 hours without giving rise to problems of encrustation, slurry stability, polymorphic form or viscosity.

U.S. Pat. No. 6,383,456 discloses an apparatus for fractionating a melt of mixed triglycerides, said apparatus comprising: a heat exchanger for supercooling the melt of mixed triglycerides; a nucleator for controlling the energy and condition of the melt of mixed triglycerides, said nucleator having an inlet and an outlet and including an agitator means, said inlet of said nucleator being connected to said heat exchanger; and a crystallizer connected to the outlet of said nucleator. In this process the nucleation stage is separated from the crystal growth stage. The examples in U.S. Pat. No. 6,383,456 are not limited to anhydrous milk fat, but include lard, tallow and palm kernel oil but do not include the fractionation of palm oil or its fractions.

EP 1 818 088A discloses a dry fractionation process for edible oils and fats comprising the steps of: melting the oil or fat to be fractionated; cooling the molten oil or fat in a crystalliser comprising a crystallisation vessel, an agitator or agitator assembly and a drive, thereby generating a slurry of crystals in a mother liquor; and subsequently separating said crystals from said mother liquor, whereby said drive provides said agitator or agitator assembly with an oscillating motion and/or a rotating motion around an axis, with the proviso that each point of said agitator or agitator assembly moves at substantially the same linear speed and in its examples describes the continuous fractionation of palm oil. Moreover, the gentle agitation intrinsic to this process surprisingly results in the formation of crystals of near uniform size, whereas in standard crystallisers, which comprise an agitator consisting of a rotating shaft with radially extending blades, several distinct populations of crystals having different sizes are obtained. This means that secondary nucleation of the crystallising melt is suppressed i.e., that no or hardly any nuclei are formed once the original nuclei started growing. Furthermore, EP 1 818 088A discloses that, contrary to what had been generally accepted, temperature homogeneity within a crystalliser is not a prerequisite for the formation of easily filterable crystals. The temperature gradient observed in Example 3 of EP 1 818 088A is such that it permits continuous operation.

A possible set-up of a continuous dry fractionation process shown in FIG. 6 of EP 1 818 088A in which there are three crystallisers in series each of which exhibiting a temperature gradient. Accordingly, the first crystalliser is fed with molten fat, and a crystal slurry ready to be filtered leaves the third one. Since the type of agitator used hardly causes vertical movement of the slurry, this set-up approaches a plug flow situation.

However, operating such a continuous dry fractionation process over an extended period of time will inevitably lead to an encrustation of solidified fat on the cooling elements used in the process, because the heat exchange surface must be markedly colder than the oil to achieve heat transfer. This causes their cooling capacity to decrease. Ultimately, the encrustation will be such that the cooling capacity will be insufficient and necessitate the interruption of the fractionation process to remove the solidified fat from said cooling elements. Therefore, the set-up of three crystallizers in series depicted in FIG. 6 of EP 1 818 088A permits in practice only a semi-continuous dry fractionation.

A plug flow is also aimed for in the continuous dewaxing process of vegetable oils and the same encrustation is also observed in this process. Oils like sunflower seed oil can contain variable amounts of waxes (esters between fatty acids and fatty alcohols) some of which have melting points above 70° C. These can cause the oil to become cloudy on cooling and since this is deemed to be undesirable, the high-melting waxes are removed by cooling the oil, thereby allowing these waxes to crystallise so that they can be removed by filtration. In comparison with the dry fractionation of edible oils and fats, the dewaxing process is quite simple. The molecules to be crystallised are less complex; they are quite different from the solvent (triglyceride oil) and to facilitate filtration, a filter aid is invariably used.

In continuous dewaxing such a plug flow is generally realised by using a crystalliser that is compartmented. Warm oil with dissolved waxes is fed at the top and oil with wax crystals leaves the vessel at the bottom and the temperature profile along the vessel remains the same. However, such vessels tend to suffer from encrustation of the cooling coils in the bottom of the vessel by wax deposits. These deposits decrease heat transfer and shift the cooling load towards the top of the vessel. This causes the oil in the top compartment to become so cold that freshly added oil is strongly undercooled so that many small wax crystals are formed. These require more filter aid than wax crystals that have been formed by slowly cooling the oil from above its cloud point to below its cloud point. Encrustation of cooling coils should therefore be avoided.

SUMMARY OF THE INVENTION

It is therefore an object of the invention to provide a continuous dry fractionation process that can adequately cope with encrustation problems.

It is an advantage of the continuous dry fractionation process of the present invention that a continuous dry fractionation process is provided that can be integrated in an edible oil refinery and thereby reduce energy requirements and save on infrastructure.

It is a further advantage of the continuous dry fractionation process of the present invention that the investment required for a given fractionation capacity is reduced.

It is also an advantage of the continuous dry fractionation process of the present invention that fractions with more consistent and improved properties are obtained.

It is yet a further advantage of the continuous dry fractionation process of the present invention that a higher olein yield in obtained in comparison with a batch process.

Surprisingly the encrustation encountered with some products using the process of EP 1 818 088A can be effectively dealt by interrupting the flow of cooling medium through the heat exchanger and at least partially melting this encrustation e.g., by electrically heating the heat exchanger or pumping hot water or blowing steam through the heat exchangers without interrupting the continuous operation of the process. This is not a measure that a person skilled in the art would contemplate taking, since once cooling has started in dry fractionation, one skilled in the art would be loath to interrupt it, regarding it as sacrosanct.

It has surprisingly been found that in a first aspect of the present invention, the above objects can be realised by a continuous process for the dry fractionation of edible oils and fats using one or more crystallisers in series, said process comprising the steps of:

a) providing molten fat;

b) continuously feeding said molten oil or fat to the first of the one or more crystallisers in series in which the fat is gradually cooled by using heat exchangers containing a cooling medium so that a crystal slurry is formed, each of said one or more crystallisers exhibiting a temperature gradient, the temperature at the point where the molten or partially crystallised fat enters one of the crystallisers being higher than that at the point where the slurry leaves that crystalliser;

c) continuously withdrawing said slurry from the last of said one or more crystallisers;

d) separating said crystal slurry by filtration in a filter cake and a filtrate; wherein said process further comprises the step of at least partially melting fat encrustations deposited on said heat exchangers.

In a preferred embodiment of the first aspect of the present invention, the process further comprises the step of continuously cooling said molten fat in a cooler to a temperature above the cloud point of said fat before entry of said molten fat into the first of said one or more crystallisers, said cooler comprising at least one heat exchange element, which may be integral or separate.

A second aspect of the present invention is an oil fraction produced by the process of the first aspect of the present invention.

Particular and preferred aspects of the invention are set out in the accompanying independent and dependent claims. Features from the dependent claims may be combined with features of the independent claims and with features of other dependent claims as appropriate and not merely as explicitly set out in the claims.

Although there has been constant improvement, change and evolution of devices in this field, the present concepts are believed to represent substantial new and novel improvements, including departures from prior practices, resulting in the provision of more efficient, stable and reliable devices of this nature.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention.

DETAILED DESCRIPTION OF THE INVENTION

The present invention will be described with respect to particular embodiments and with reference to certain drawings but the invention is not limited thereto but only by the claims.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term “comprising”, used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof.

Reference throughout this specification to “one embodiment” or “an embodiment” means that a particular feature, structure or characteristic described in connection with the embodiment is included in at least one embodiment of the present invention. Thus, appearances of the phrases “in one embodiment” or “in an embodiment” in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

The oil or fat to be used in the process according to the invention can be of vegetable or animal origin. Examples of vegetable oils and fats are palm oil, various palm oil fractions, shea butter, mango kernel fat, hydrogenated vegetable oils such as soybean oil or rapeseed oil (canola) and even lauric fats such as palm kernel oil and coconut oil. The process of the invention can also be used for the winterisation, i.e., the removal of high melting triglycerides from for instance cottonseed oil. Examples of animal oils and fats are oils and fats that are already fractionated such as lard, beef tallow, mutton tallow, anhydrous milk fat, chicken fat, and fish oil.

The oil or fat to be fractionated is preferably at least partially refined. Accordingly, it should no longer contain the gums that are present in the crude oil since these can interfere with the crystallisation and the free fatty acid content should preferably also be reduced to below 0.5 wt % by alkali refining or vacuum steam stripping.

The fat to be fractionated according to the invention should be molten. It may be somewhat cloudy but its solid fat content should preferably be below 2 wt %, and more preferably below 1 wt %. One way of introducing the molten fat into the first of one or more crystallisers is to pump it from a land tank or day tank. If the fractionation plant forms an integrated part of a refinery, a small intermediate storage tank will suffice. In edible oil fractionation, it is customary to raise the temperature of the fat to be fractionated some 10° C. above its melting point. This heating step can also precede the process according to the invention, but if it is found to be unnecessary and/or if its omission is found to be beneficial, the resulting process can still fall within the scope of the invention.

If the temperature of the fat being pumped from storage is more than 10° C. above its cloud point, it can be advantageous to cool the fat to just above its cloud point in a simple cooler. Cooling to below its cloud point for longer periods of time is not recommended since this may lead to a deposit of fat crystals in the cooler. If the temperature of the fat is below its cloud point for a short period, and this leads to a deposit, this deposit will be melted and removed by the continuous flow of oil once its temperature is sufficiently high to melt the high melting triglycerides that constitute the deposit; this can be several degrees above the cloud point. In the process according to the invention, temporary interruption of the cooling medium flow may also expedite the at least partial melting of any crystalline deposits.

Whereas the crystalliser disclosed in U.S. Pat. No. 5,874,599 maintains a substantially uniform temperature throughout the entire vessel, each of the one or more crystallisers to be used in the process according to the invention must show a temperature gradient. At the point where the molten or partially crystallised fat, which may be the result of the fat having been cooled in the cooler, enters the crystalliser, its temperature will be higher than at the point where the slurry leaves that crystalliser. In general, the crystalliser will be filled from the top and the crystal slurry will leave the vessel at its lowest point but the process according to the invention is not limited to this set-up. Establishing this gradient places some demands on the design of the crystalliser and especially its agitator.

Whereas standard crystallisation vessels used to fractionate edible oils and fats incorporate an agitator that comprises a rotating shaft onto which agitator blades have been fitted in such a way that on rotation, these blades exert a vertical force onto the surrounding slurry, the agitator to be used in the process according to the invention should preferably not exert such a vertical force and only ensure contact between the crystal slurry and the heat exchangers present in the crystallisation vessel. In this respect the agitator type disclosed in EP 1 818 088A is very suitable; it is therefore included by reference in its entirety. It also has the advantage that its linear speed is low and this suppresses secondary nucleation and thereby leads to the formation of a homogeneous crystal population. In one of the embodiments disclosed in EP 1 818 088A, the agitator itself also acts as heat exchanger. In another embodiment, the agitator moves in between stationary heat exchangers. Both embodiments are suitable for the process according to the invention.

Another type of agitator that has been found to be most useful in the process according to the invention is in GB 2 053 019. Like the agitators disclosed in EP 1 818 088A, it provides a gentle agitation and does not exert any net vertical force. Moreover, it can easily be fitted inside a tall crystallisation vessel.

More standard, rotating agitators can also be used in the process according to the invention provided the agitator rotates slowly, and the agitator blades are not tilted and only provide a radial force on the surrounding crystal slurry to force the slurry in the direction of the heat exchangers. These heat exchangers can be spirally wound coils as present in many existing crystallisers. This means that these crystallisers can be retrofitted to accommodate the process according to the invention by replacing the agitator blades.

Although cooling surfaces and agitators can be designed so as to minimize encrustation, this often involves high liquid speeds. In the continuous dry fractionation process of oils according to the invention, these high speeds have to be avoided since they have been found to lead to secondary nucleation, non-uniform crystal sizes, slow filtration and high residual oil content in the filter cake. Accordingly, the process of the invention comprises means to at least partially melt fat encrustations that have been deposited on the cooling surfaces of said heat exchangers in said one or more crystallisers and the cooling surfaces of the at least one heat exchange element in said cooler.

One method to remove these encrustations comprises means to heat the cooling surfaces of said heat exchangers and/or the at least one heat exchange element of said cooler electrically. To avoid simultaneous heating of the cooling medium, this is preferably drained from the heat exchanger and/or the at least one heat exchange element of said cooler before any current is supplied to the electrical heating system.

Other means comprise the possibility of heating by the Joule effect, induction and injecting a small amount of heating medium, such as for example hot water or steam, into the heat exchangers and/or the at least one heat exchange element of the cooler that suffices to loosen any encrustation that might have formed on these heat exchangers and/or the at least one heat exchange element of said cooler. Injecting this small amount of heating medium will also melt and thereby eliminate embryonic encrustations that are hardly visible to the naked eye but that serve as a starting point for crystal growth. Removing these embryonic encrustations requires less heat and less time than loosening visible encrustations by at least partially melting the crystals that make them adhere to the heat exchanger surface. Because embryonic encrustations will hardly show up by temperature difference determinations, their removal is preferably actuated by a programmable timer. Complete melting of the encrusted crystals has been found not to be necessary. Once they do no longer adhere to the heat exchanger outer surface, they are dislodged by the slowly agitated oil slurry. Partial melting of the encrustation by such shock heating has the advantage that it requires less heat and less time than complete melting and has the additional advantage that it does not noticeably heat the bulk of the slurry contained in the crystalliser.

A person skilled in the art will be familiar with several ways of realising this short burst of heating medium e.g., hot water or steam. Preferably, the cooling medium (e.g., cooling water) is first of all drained from the heat exchangers and/or the at least one heat exchange element of said cooler so that when steam is blown into the empty elements, it condenses on the inner surface of these elements, heats their surface and causes adhering crystals to melt at least partially.

The sequence of draining, heating medium injection (or electrical heating) and reverting to cooling mode is preferably automated and can be triggered by a low temperature difference between ingoing and outgoing cooling water or by an increase of the temperature difference between oil and the cooling water caused by a drop of the rate of heat exchange. It can also be programmed on a regular time basis and thereby focus on embryonic encrustations that do not show up by measuring temperature differences. If the heat exchangers or heat exchange elements consist of long, spirally wound coils, it may be advantageous to divide these into several superimposed, smaller units, which is an aspect to be taken into account when retrofitting an existing crystalliser to the process according to the invention. Draining such smaller units is faster and can be limited to that unit that happens to be encrusted. Moreover, the use of several smaller units facilitates the temperature control in the crystalliser. Accordingly, the temperature of the cooling medium, e.g., cooling water, in the top unit can be controlled at a higher level than at lower units. In new crystallisers, the size (surface) of the various heat exchangers and heat exchange elements can take into account how much heat has to be removed in that particular section of the crystalliser. In the top section of a tall crystalliser or the first of one or more crystallisers, mainly sensible heat has to be removed to lower the temperature of the molten fat to below its cloud point. When the fat starts to crystallise, the crystals are initially quite small which means that they do not grow very fast. Accordingly, cooling should be such that it does not lower the temperature too fast since this will lead to excessive supersaturation and increase the risk that new nuclei are formed. In the section where the main crystallisation takes place, the heat exchange capacity of the vessel can be larger since this is where most of the latent heat of crystallisation will be liberated and has to be removed.

To encourage a plug flow of the fat being crystallised it can be made to flow from one crystalliser to the next as shown in FIG. 6 of EP 1 818 088A. If a tall vessel is used as crystalliser, this can be compartmented but since the agitation does not induce any vertical movement, this compartmentation is far from mandatory. In fact, in such tall crystallisers, the crystals formed high up should be free to sink slowly to the bottom and grow while doing so because the temperature decreases from top to bottom in the crystalliser.

When several crystallisers in series are used in the process according to the invention, the crystals can only sink to the bottom of each separate crystalliser. The crystal slurry has to be transferred to the next crystalliser and provided they are positioned the one slightly above the other, this transfer can be by gravity. If this is ineffective, a pump is needed for the transfer. Care should be taken to choose a pump that does not crush the fat crystals.

The slurry leaving the crystalliser has to be separated by filtration into a stearin fraction and an olein fraction. If the filtration is a batch process as is the case of the membrane filter press, a small intermediate storage vessel is needed. To prevent the slurry from settling, this vessel is preferably provided with an agitator that will keep the crystals in suspension; this also ensures a constant viscosity feed to the filter press. If the filtration system operates continuously, the intermediate storage vessel is superfluous.

The filter cake has to be melted before the stearin can be pumped to the stearin storage tank. When the fractionation plant forms part of a refinery complex, the heat required for the melting of the stearin may be provided at little cost by the refinery in a similar way as the heat for melting encrusted crystals can originate from this refinery. One source of heat could be the latent heat set free in deodoriser scrubbers. Normally, the scrubber condensate is cooled with cooling water in a heat exchanger before being sent to scrubber distillate storage. Instead, the heat exchanger could be fed with boiler feed water to generate low-pressure steam that can be profitably used to melt the stearin filter cake.

Operating the process according to the invention and producing fractions within specification means that crystalliser throughput and cooling medium temperatures and flow rate have to be carefully matched. No precise rules can be given in this respect, but it has been found that starting with a lowish feed rate of molten fat e.g. less than 75% of the rated capacity and gradually increasing this feed rate is an effective way of commissioning the process according to the invention. During this commissioning, the temperature of the cooling medium flowing through the heat exchanger in the top compartment or the first of the one or more crystallisers should be somewhat below the temperature of the molten fat fed to this compartment or crystalliser. The temperature of the cooling medium flowing through the heat exchanger in the bottom compartment or the last of the one or more crystallisers should be just below the filtration temperature. The other cooling medium temperatures should be in between. Lowering these cooling medium temperatures will lead to more heat being removed and this can be matched by increasing the feed rate until filtration problems arise and/or fraction properties start to deviate from target.

In general it can be said that surprisingly, the process according to the invention is more productive on a crystalliser volume basis and leads to a better selectivity than the batch processes of the prior art. It also saves on energy in comparison with these batch processes since the crystalliser has no longer to be heated and cooled but can maintain its operation temperature thanks to the continuous operation. The occasional encrustation encountered with some products can be effectively dealt with out seriously interrupting the continuous operation of the process according to the invention. It is also possible to use the one or more crystallisers of the process according to the invention in a batch mode but then, there is little need for the removal of encrustations. It can be useful though during a period of frequent stock changes.

EXAMPLE 1

The example relates to an experiment using a crystalliser according to FIG. 4C in EP 1 818 088A. The capacity of the crystalliser was 35 tons, the liquid level was 3.3 m above the vessel floor and the cooling surface was 5.5 $m^2$ per ton of oil. The crystalliser was filled with palm oil having an iodine value (IV) of 51.6 by pumping the oil from a storage tank in which the oil temperature was maintained at 60° C. through a plate heat exchanger that cooled the oil to just below 40° C.

The experiment started as a batch process but when the oil temperature at the crystalliser outlet had reached about 26° C., the crystallisation process was made continuous by feeding oil with a temperature of about 40° C. into the top of the crystalliser at a rate of 7 to 8 tons per hour and allowing a crystal slurry with a solid fat content (SFC) of about 7 wt % to flow from the bottom of the crystalliser to an intermediate storage vessel feeding the batch membrane filter press. The experiment was continued for 63 hours during which period 14 filtrations were carried out. The olein yield was 84 wt % and its iodine value (IV) varied between 55.6 and 57.5.

The temperature of the slurry leaving the intermediate storage vessel varied between 24.7° C. and 25.3° C., and it was 25.1° C. on average. Its average SFC was 8.4 wt %. This is slightly higher than the average SFC of the slurry leaving the crystalliser, which was 7.3 wt %. This slight increase in solid fat content may be due to the slurry leaving the crystalliser being slightly undercooled and/or the fact that the slurry temperature was reduced from an average value of 26.1° C. to an average value of 25.1° C. in the intermediate storage vessel.

The cooling water temperature difference of the plate heat exchanger was monitored and when this markedly decreased, the cooling water flow was interrupted so that warm oil of 58-60° C. flowed through the heat exchanger and melted any crystal deposit in the heat exchanger. A cooling water flow interruption of 2 minutes was found to suffice for complete elimination of any deposit, and the hot oil entering the crystalliser during this 2 minute period did not disturb its operation. During the 63 hours of continuous operation, the cooling water flow was interrupted 5 times.

Crystal deposits on the cooling elements in the crystalliser have also been melted by passing hot water through them for a period of 10 minutes. This was done two times in the course of the entire experiment. Visual inspection of the cooling elements after the experiment showed them to be free from any serious encrustation. This means that the continuous operation could have been extended.

The experiment shows a number of advantages of the process according to the invention. The melting of crystal encrustations hardly interrupts the functioning of the crystalliser and surprisingly allows it to operate continuously and steadily over a long period of time. In comparison with the batch process operated in a similar crystalliser, the continuous process has a throughput that is 20 to 25% higher. Energy usage is up to 30% reduced, and surprisingly, less filter capacity is required for the continuous process according to the invention because the resulting crystal cakes exhibit significantly higher permeability during filtration. Additionally, during cake compaction in the filter, the crystal cakes display higher compressibility and up to 3 wt % more olein can be recovered (on 100% cake basis), which has also economic advantages.

EXAMPLE 2

In this example, two crystallisers as described in Example 1 were used in series. The first crystalliser was filled with palm oil having an iodine value of 51.6 by pumping the oil from a storage tank in which the oil temperature was maintained at 55° C. through a plate heat exchanger that cooled the oil to 36° C.

The experiment started as a batch process, but when the oil temperature at the crystalliser outlet had reached about 26° C., the crystallisation process was made continuous by continuously feeding oil with a temperature of about 36° C. into the top of the first crystalliser at a rate of 3 to 3.5 tons per hour and allowing a crystal slurry with a solid fat content (SFC) of about 13-15 wt % and a temperature of about 20° C. to flow from the bottom of the first crystalliser into the top of the second crystalliser, where it crystallised further to yield a slurry with a solid fat content (SFC) of about 23-26 wt % and a temperature of about 15-16° C. at the outlet of the second crystalliser. From there the slurry was transferred continuously to an intermediate storage vessel feeding the batch membrane filter press. The experiment was continued for 190 hours during which period 38 filtrations were carried out. The olein yield was 61.3 wt % and its IV varied between 61.5 and 63.4.

The temperature of the slurry leaving the intermediate storage vessel varied between 14.8° C. and 15.4° C., and it was 15.1° C. on average. Its average SFC was 26.3 wt %. This is slightly higher than the average SFC of the slurry leaving the second crystalliser, which was 24.4 wt %. This slight increase in solid fat content is similar to what was observed in Example 1.

Like in Example 1, the cooling water temperature difference of the plate heat exchanger was monitored and when this markedly decreased, the cooling water flow was interrupted so that warm oil of 55-58° C. flowed through the heat exchanger causing any crystal deposit in the heat exchanger to melt. Again, a cooling water flow interruption of 2 minutes was found to suffice for complete elimination of any deposit and the hot oil entering the crystalliser during this 2 minute period did not disturb its operation. During the 190 hours of continuous operation, the cooling water flow was interrupted 12 times.

Passing hot water through them for a period of 15 minutes could again melt crystal deposits on the cooling elements in the crystalliser. During the 190 hours of continuous operation, the hot water was passed through the bundles 7 times.

This example therefore illustrates that the process according to the invention can be successfully carried out with two crystallisers in series. It also highlights the product advantages of the process according to the invention.

Table 1 below summarises the analytical and performance data of both examples.

TABLE 1

| Example 1 | Batch | | Continuous | |
|---|---|---|---|---|
| Crystallization batch time (hrs) | ~6.6 h | | | |
| Net average residence time (hrs) | | | ~5 h | |
| SFC of the slurry (wt %) | ~8.7 | | ~8.4 | |
| | Stearin | Olein | Stearin | Olein |
| Mettler cloud point[1] (° C.) | | 9.8 | | 9.4 |
| IV (Wijs) | 32.5 | 56.2 | 30.1 | 56.3 |
| PPP[2] (wt % by HPLC) | NA | 0.75 | NA | 0.32 |
| Yield (wt %) | 18 | 82 | 16.4 | 83.6 |
| SFC of the cake (wt %) | 58.8 | | 61.3 | |
| Filter Load (ton slurry/$m^3$ filter volume) | 2.6 | | 3.25 | |
| **Example 2** | **Batch** | | **Continuous** | |
| Crystallization batch time (hrs) | ~20 | | | |
| Net average residence time (hrs) | | | ~18 | |
| SFC of the slurry (wt %) | ~23 | | ~26 | |
| | Stearin | Olein | Stearin | Olein |
| Mettler cloud point[1] (° C.) | | 3.4 | | 3.1 |
| IV (Wijs) | 37.3 | 61.7 | 35.1 | 62.7 |
| TAG[3] (wt % by HPLC) | | | | |
| POP[4] | 38.8 | 20.4 | 42.1 | 18.6 |
| PPP | 6.9 | 3.8 | 7.6 | 3.4 |
| StStSt[5] | 17.0 | N.D. | 17.3 | N.D. |
| Yield (wt %) | 39.8 | 60.2 | 38.8 | 61.2 |
| SFC of the cake (wt %) | 57.8 | | 67.0 | |
| Filter Load (ton slurry/$m^3$ filter volume) | 1.25 | | 1.46 | |

[1]cooling rate of 3° C. per minute
[2]PPP = tripalmitate
[3]TAG = triacylglycerol
[4]POP = oleyldipalmitoylglycerol
[5]StStSt = tristearoate Table 1 further illustrates the surprising observation that all performance parameters of the continuous fractionation process according to our invention and all products properties obtained by the process according to our invention are improved compared to the batch fractionation process carried out in the same crystalliser vessel.

The invention claimed is:

1. A continuous process for the dry fractionation of edible oils and fats using one or more crystallisers in series, said process comprising the steps of:

a) providing a molten fat, b) continuously feeding said molten oil or fat to the first of said one or more crystallisers in series in which the fat is gradually cooled by using heat exchangers containing a cooling medium so that a crystal slurry is formed, each of said one or more crystallisers exhibiting a temperature gradient, the temperature at the point where the molten or partially crystallised fat enters one of the crystallisers being higher than that at the point where the slurry leaves that crystalliser;

c) continuously withdrawing said slurry from the last of said one or more crystallisers, d) separating said crystal slurry by filtration in a filter cake and a filtrate, wherein said process further comprises the step of at least partially melting fat encrustations deposited on said heat exchangers.

2. The continuous process according to claim 1, wherein said continuous process further comprises the step of continuously cooling said molten fat in a cooler to a temperature above the cloud point of said fat before entry of said molten fat into the first of said one or more crystallisers, said cooler comprising at least one heat exchange element.

3. The process according to claim 2, in which the at least partial melting of fat encrustations in the cooler is effectuated by temporarily interrupting the flow of said cooling medium to the at least one heat exchange element of said cooler or electrically heating the surface of the at least one heat exchange element of said cooler.

4. The process according to claim 3, in which the temporary interruption of the cooling medium flow is actuated by a temperature difference switch.

5. The process according to claim 3, in which the temporary interruption of the cooling medium flow is actuated by a programmable timer.

6. The process according to claim 1, in which said step to at least partially melt fat encrustations comprises electrical heating of the surface of said heat exchangers.

7. The process according to claim 1, in which a heating medium that is sufficiently hot to at least partially melt fat encrustations that may have been deposited in the heat exchangers used in step b) and at least partial melt fat encrustations on the at least one heat exchange element of said cooler is made to flow through said heat exchangers and/or the at least one heat exchange element of said cooler.

8. The process according to claim 7, in which said heat exchangers and/or the at least one heat exchange element of said cooler are at least partially drained before a heating medium is made to flow through said heat exchangers and/or the at least one heat exchange element of said cooler.

9. The process according to claim 7, in which said heating medium is steam.

10. The process according to claim 9, in which said steam has been generated in the scrubber of a vacuum stripping unit in a nearby refinery complex.

11. The process according to claim 7, in which said heating medium is heated water.

12. The process according to claim 11, in which said heated water has been heated by having been used as a cooling medium in a nearby refinery complex.

13. The process according claim 7, in which the switch from cooling medium to heating medium in said heat exchangers and/or the heat exchange elements of said cooler is actuated by a decrease in the temperature difference between the outgoing and incoming cooling medium.

14. The process according to claim 7, in which the switch from cooling medium to heating medium is actuated by a programmable timer.

15. The process according to claim 1, in which the agitators of the one or more crystallisers hardly exert a net vertical force on the crystalliser contents.

16. The process according to claim 1, in which agitators also acts as a heat exchanger.

17. The process according to claim 1, in which the construction of the one or more crystallisers promotes a plug flow.

18. The process according to claim 17 in which the one or more crystallisers is compartmented.

19. The process according to claim 1, in which the stearin cake resulting from the filtration of the final crystal slurry is melted by a heating medium recovered from upstream oil treatments in a nearby refinery complex such as degumming and/or deodorisation.

* * * * *